United States Patent [19]

Burnie

[11] Patent Number: 5,985,277
[45] Date of Patent: Nov. 16, 1999

[54] ANTIBODIES TO BACTERIAL STRESS PROTEINS

[75] Inventor: Peter James Burnie, Alderley Edge, United Kingdom

[73] Assignee: The Victoria University of Manchester, Manchester, United Kingdom

[21] Appl. No.: 08/878,844

[22] Filed: Jun. 19, 1997

Related U.S. Application Data

[62] Division of application No. 08/409,901, Mar. 22, 1995, abandoned, which is a continuation of application No. 07/842,347, filed as application No. PCT/GB91/01252, Jul. 25, 1991, abandoned.

[30] Foreign Application Priority Data

Jul. 25, 1990 [GB] United Kingdom .................. 9016315

[51] Int. Cl.$^6$ ........................ A61K 39/395; A61K 39/40; C07K 16/00; C07H 21/04
[52] U.S. Cl. ..................................... 424/139.1; 424/141.1; 424/151.1; 424/166.1; 530/387.9; 530/388.4; 530/389.5; 536/23.7
[58] Field of Search ............................. 530/387.9, 388.4, 530/389.5; 424/166.1, 139.1, 141.1, 151.1; 536/23.7

[56] References Cited

U.S. PATENT DOCUMENTS 5,288,639  2/1994  Burnie et al. .

OTHER PUBLICATIONS

Plotkin et al (ed), "Vaccines", published by WB Saunders Company (Philadelphia) pp. 568–575, 1988.
Stein et al. Science 261:1004–1012, 1993.
Burgess et al. Journal of Cell Biology vol. 111, pp. 2129–2138, Nov. 1990.
Lazar et al. Molecular and Cellular Biology vol. 8, No. 3, pp. 1247–1252, Mar. 1988.
Tizard, I (Ed.) "An Introduction to Veterinary Immunology", published by W.B. Saunders Co. (Phil) in 1982 p. 32.
Clark et al. Characterization of the antibody response in Corynebacterium jeikeium sp. Epidemol Infect.; 105(2) 229–236 1990.
Young, R.A. Stress Proteins as Immune Targets in Bacterial and Parasitic Infections, pp. 123–130. See In Immune Recognition and Evasion, Vander Pleog Harlow and Lane Antibodies, A Laboratory Manual 1988 pp. 553–612.
Jackman et al. Characterization of Corynebactereium Group JK by Whole–Cell Protein Patterns J. Gen Microbial 132 1911–15 1986.
Christman et al. Positive Control of a Regulon for Defenses against Oxidative Stress and Some Heat Shock Proteins in S.typhimurium Cell 41:753–62 1985.
Morgan et al. Hydrogen Peroxide–inducible proteins in Salmonella typhimurium overlap with heat shock and other stress proteins PNAS 83(21):8059–63 1986.
R. Matthews et al: "Cloning of a DNA sequence encoding a major fragment of the 47 kilodalton stress protein stress protein homoloque of Candida albicans" Chemical Abstracts, vol. 111, No. 13, Sep. 1989, p. 199.
H. Yamaguchi et al: "Yarsinia enterocolitica immunodominant 60 KDa antigen, common to a broad range of bacteria is a heat–shock protein", Biological Abstracts, vol. 90, 1990 Abstract # 54993.
C.K. Stover et al: "Molecular cloning and sequence analysis of the Sta58 major antigen gene of Rickettsia tsutsugamushi: sequence homology and antigenic comparison of Sta58 to the 60–kilodalton family of stress proteins", Infection and Immunity, vol. 58, No. 5, May 1990 pp. 1360–1368.
J.L.Brissette et al: "Phage shock protein, a stress protein of Escherichia coli", Proceedings of the National Acadamy of Sciences, vol. 87, No. 3, Feb. 1990, Biochemistry, pp. 862–866.

Primary Examiner—Anthony C. Caputa
Assistant Examiner—Mark Navarro
Attorney, Agent, or Firm—Pillsbury Madison & Sutro LLP

[57] ABSTRACT

The present invention relates to antibodies to a purified stress protein of 86 Kd and fragments thereof isolated from the genus Corynebacterium. Particular fragments include those with apparent molecular weights of 50 Kd and 52 Kd. The stress protein has been found to be an immunodominant conserved antigen. Patients with Corynebacterium jeikeium septicemia or endocarditis have antibody to the 52 Kd breakdown product. The protein cross-reacts with a peptide antigen KVIRKNIVKKMIE using a mouse monoclonal antibody against the peptide. The antibodies are useful for diagnosis and treatement of Corynebacterium infections and diseases.

5 Claims, 4 Drawing Sheets

ANTIBODIES TO BACTERIAL STRESS PROTEINS

This application is a division of application Ser. No. 08/409,901, filed Mar. 22, 1995, now abandoned, which is a continuation of application Ser. No. 07/842,347, filed May 26, 1992, now abandoned, which was made under 35 USC §371, based on PCT/GB91/01252, filed Jul. 25, 1991, which in turn is based on Application No. 9016315.5 filed Jul. 25, 1990 in Great Britain.

FIELD OF THE INVENTION

This invention relates to bacterial stress proteins, to inhibitors thereof and to their use in medicine and for diagnosis.

BACKGROUND TO THE INVENTION

Environmental stress can induce an increase in the rate of synthesis of so-called heat shock, or stress, proteins in both procaryotic and eucaryotic cells [see for example Schlesinger et al (eds) in Heat Shock from Bacteria to Man, Cold Spring Harbor Laboratory, Cold Spring Harbor, N.Y. (1972)]. Although the function of stress proteins has yet to be finally resolved, some have been reported to participate in assembly and structural stabilisation of certain cellular and viral proteins, and their presence at high concentration may have an additional stabilising effect during exposure to adverse conditions.

Many pathogenic organisms have been shown to produce stress proteins [see for example Young D., et al, Proc. Natl. Acad. Sci. USA, 85, 4267–4270 (1988)]. The proteins are thought to be produced in response to the stress of infection to help protect the invading pathogen. Thus, for example, the ability to produce stress proteins has been implicated in the survival of bacterial pathogens within macrophages [Christmas, M. Y., et al, Cell, 41, 753–762 (1985) and Morgan R. W., et al, Proc. Natl. Acad. Sci. U.S.A, 83, 8059–8063 (1986)].

It has been suggested that the presence of stress proteins in a variety of human pathogens indicates that the stress response is a general component of infections, and that stress proteins should be considered among candidates for subunit vaccines [Young, D. et al ibid].

The Coryneform bacteria are common inhabitants of healthy human skin and mucous membranes. Some are known pathogens, for example the type species *Corynebacterium diphtheriae* causes diphtheria in man. Another species, *Corynebacterium jeikeium* causes septicaemias in neutropenic patients [see for example, Bande, K. R., et al, Ann. Intern. Med., 85, 423–426 (1976)], and *C.jeikeium* infection has been associated with endocarditis [Jackman, P. J., et al, Syst. Appl. Microbial., 9, (1–2), 83–90 (1987)]. These *C.jeikeium* species are characterised by being catalase-positive, oxidase-negative, fermentative Gram positive aerobic rods which do not reduce nitrate [Riley, P. S., et al, J. Clin, Microbial., 9, 418–424, (1979)]. They differ from other coryneforms by being highly resistant to antibiotics, including ampicillin, cephalothin, chloramphenicol, erythromycin, gentamicin, penicillin G, streptomycin and tetracycline [Jackman, P. J., Pelczyneka, S., J. Gen. Microbial., 132, (Pt.7), 1911–1915 (1986)].

Conventional therapy for a *C.jeikeium* infection is systemic vancomycin, which is potentially nephrotoxic. This mitigates against its blind use in pyrexial neutropenic patients, so that it has become important to develop a marker of *C.jeikeium* infection. There is also a need for a method of treating *C.jeikeium* infection, particularly in neutropenic patients, which avoids the damaging side effects associated with conventional therapy.

SUMMARY OF THE INVENTION

We have now found that recovery from *C.jeikeium* septicaemia in humans is associated with the production of antibodies of both IgN and IgG classes against a protein of apparent molecular weight 52 Kd. Further tests using antibodies raised against a known fungal stress protein have shown that the 52 Kd protein is a breakdown product of an 86 Kd antigen analogous to the 90 Kd heat shock protein of *Candida albicans*. We have used this discovery to develop means for the improved diagnosis and treatment of Corynebacterium infections and diseases caused by related Gram positive bacteria.

Thus according to one aspect of the invention we provide a bacterial stress protein having an apparent molecular weight of around 86 Kd or a fragment or an analogue thereof.

The term "apparent molecular weight" as used herein is intended to mean the apparent molecular weight as determined by 10% sodium dodecyl sulphate-polyacrylamide gel electrophoreisis using molecular weight markers supplied by Amersham International PRESTAINED RAINBOW MARKERS (code RPN.756).

The stress protein according to the invention may be of bacterial origin and may be obtainable, for example, from Gram-positive bacterial strains. Particular strains include those belonging to the genus Corynebacterium, for example strains of *Corynebacterium diphtheriae* or, in particular, *Corynebacterium jeikeium*, and related Corynebacterial species.

The stress protein, fragment or analogue thereof according to the invention may be a recombinant protein, fragment or analogue, i.e. a protein, fragment or analogue which has been produced using recombinant DNA techniques.

A fragment of a stress protein according to the invention may be any shorter breakdown product of the protein or an analogue thereof. Particular fragments include those with apparent molecular weights of around 52 Kd or 50 Kd.

Analogues of a stress protein according to the invention include those proteins wherein one or more amino acids of the protein is replaced by another amino acid, providing that the overall functionality of the protein is conserved.

A stress protein according to the invention may be obtained in a purified form, and thus according to a further aspect of the invention we provide a substantially pure bacterial stress protein having an apparent molecular weight of around 86 Kd or a fragment or an analogue thereof.

The term substantially pure is intended to mean that the stress protein according to the invention is free from other proteins of bacterial origin. In the various aspects of the invention described hereinafter it is to be understood that a reference to the bacterial stress protein also includes substantially pure preparations of the protein.

A stress protein according to the invention may be further characterised by one or more of the following features:

(1) it is an immunodominant conserved antigen;

(2) patients with *C.jeikeium* septicaemia on recovery have antibody to a 52 Kd breakdown product of the stress protein; and (3) patients with *C.jeikeium* endocarditis have antibody to a 52 Kd breakdown product of the stress protein;

(4) it cross-reacts with a peptide antigen KVIRKNIVKK-MIE (SEQ ID NO: 1) using mouse monoclonal antibody against the peptide antigen; and (5) cross-reaction of the stress protein and mouse monoclonal antibody against the peptide antigen KVIRKNIVKKMIE (SEQ ID NO:1) is neutralised by peptide KVIRKNIVKKMIE (SEQ ID NO:1).

Throughout this document peptides are identified using a single letter to represent each separate amino acid. Each letter is the conventional single letter symbol used for amino acids.

A stress protein according to the invention has a number of uses. Thus, for example, the protein may form the basis of a diagnostic test for bacterial infection, for example an immunological test such as an enzyme-linked immunosorbent assay, a radioimmunoassay or a latex agglutination assay, essentially to determine whether antibodies specific for the protein are present in a host organism. The test may be generally performed by contacting body fluid from the host with the stress protein and detecting any complexed material.

In another use, the stress protein according to the invention may be employed, using conventional techniques, for screening to obtain activity inhibiting agents for use in the teatment of bacterial infections. Such a screening method forms a further aspect of the invention.

In a further use, the stress protein according to the invention is particularly well suited for the generation of antibodies. Thus according to a further aspect of the invention we provide a bacterial stress protein having an apparent molecular weight of 86 Kd or a fragment or an analogue thereof, for use as an immunogen.

Standard immunological techniques may be employed with the stress protein in order to use it as an immunogen. Thus, for example, any suitable host may be injected with the protein and the serum collected to yield the desired polyclonal anti-stress protein antibody after purification and/or concentration. Prior to injection of the host the stress protein may be formulated in a suitable vehicle and thus according to a further aspect of the invention we provide a composition comprising a fungal stress protein having an apparent molecular weight of 86 Kd or a fragment or an analogue thereof together with one or more pharmaceutically acceptable excipients.

For purification of any anti-stress protein antibody, use may be made of affinity chromatography employing an immobilised stress protein of the invention as the affinity medium. Thus according to another aspect of the invention we provide a bacterial stress protein having an apparent molecular weight of 86 Kd or a fragment or an analogue thereof, covalently bound to an insoluble support.

The use of the stress proteins according to the invention as immunogens for the production of antibodies generates one type of inhibitor of the action of the protein. Generally, inhibitors of the stress proteins are potentially useful in the diagnosis, and in particular the treatment, of bacterial infections and provide a further feature of the invention. Inhibitors include any antagonists of the action of the stress proteins or agents which prevent their production, and in particular include those which may be used in the treatment of bacterial infections. Suitable inhibitors include for example pharmaceutical reagents, including antibodies, and chemical analogues of the stress proteins to antagonise the action of the stress protein, and anti-sense RNA and DNA oligonucleotide analogues to prevent production of the stress protein. Suitable inhibitors may be determined using appropriate screens, for example by measuring the ability of a potential inhibitor to antagonise the action of, or prevent the production of a stress protein according to the invention or a fragment or an analogue thereof.

According to a further aspect of the invention we provide an inhibitor of a bacterial stress protein, said protein having an apparent molecular weight of 86 Kd or a fragment or an analogue thereof, for use in the diagnosis or treatment of bacterial infections.

Inhibitors may be used either alone or where appropriate in combination with other pharmaceutical agents, for example, other anti-bacterial agents or anti-fungal agents.

One particularly useful group of inhibitors according to this aspect of the invention are antibodies capable of recognising and binding to the stress proteins.

Thus, according to yet another aspect of the invention we provide an antibody specific for one or more epitopes of a bacterial stress protein having an apparent molecular weight of 86 Kd or a fragment or an analogue thereof, for use in the diagnosis or treatment of bacterial infections.

The antibody may be a whole antibody or an antigen binding fragment thereof and may in general belong to any immunoglobulin class. Thus, for example, it may be an immuniglubulin M antibody or, in particular, an immunoglobulin G antibody. The antibody or fragment may be of animal, for example mammalian origin and may be for example of murine, rat or human origin. It may be a natural antibody or a fragment thereof, or, if desired, a recombinant antibody or antibody fragment, i.e. an antibody or antibody fragment which has been produced using recombinant DNA techniques.

Particular recombinant antibodies or antibody fragments include, (1) those having an antigen binding site at least part of which is derived from a different antibody, for example those in which the hypervariable or complementarity determining regions of one antibody have been grafted into the variable framework regions of a second, different antibody (as described in European Patent Specification No. 239400); (2) recombinant antibodies or fragments wherein non-variable domain sequences have been substituted by non-variable domain sequences from other, different antibodies (as described in European Patent Specifications Nos. 120694, 125020, 171496, 173494 and 194276); or (3) recombinant antibodies or fragments possessing substantially the structure of a natural immunoglobulin but wherein the hinge region has a different number of cysteine residues from that found in the natural immunoglobulin, or wherein one or more cysteine residues in a surface pocket of the recombinant antibody or fragment is in the place of another amino acid residue present in the natural immunoglobulin (as described in International Patent Specification Nos. WO89/01974 and WO89/01782 respectively).

The antibody or antibody fragment may be of polyclonal, or preferably, monoclonal origin. It may be specific for a number of epitopes associated with the stress protein but it is preferably specific for one.

Antigen binding antibody fragments include for example fragments derived by enzymatic cleavage of a whole antibody, such as F(ab')$_2$, Fab', Fab or Fv fragments, or fragments obtained by recomginant DNA techniques, for example as described in International Patent Specification No. WO89/02465, as well as single chain antibodies, e.g. single chain Fvs.

The antibody or fragment may be cross-linked, for example as described in European Patent Specification No. 385601. Antibody or antibody fragment molecules may also be cross-linked to yield multimeric forms [for example IgG molecules may be cross-linked to form trimeric, tetrameric or larger multimeric structures], using conventional cross-linking approaches, for example by cross-linking amino acid side chains present in the molecules, and containing an amino, sulphydryl or other functional group, using a cross-linking reagent.

The antibodies according to the invention may be prepared using well-known immunological techniques employing the stress protein as antigen. Thus, for example, any suitable host may be injected with the stress protein and the serum collected to yield the desired polyclonal antibody after appropriate purification and/or concentration (for example by affinity chromatography using the immobilised stress protein as the affinity medium). Alternatively splenocytes or lymphocytes may be recovered from the stress protein injected host and immortalised using for example the method of Kohler et al, Eur. J. Immunol. 6, 511, (1976), the resulting cells being segregated to obtain a single genetic line producing monoclonal anti-fungal stress proteins. Antibody fragments may be produced using conventional techniques, for example by enzymatic digestion, e.g. with pepsin [Parham, J. Immunol, 131, 2895 (1983)] or papain [Lamoyi and Nisonoff, J. Immunol, Meth., 56, 235, (1983)]. Where it is desired to produce recombinant antibodies according to the invention these may be produced using for example the methods described in European Patent Specifications Nos. 171496, 173494, 194276 and 239400.

Antibodies according to the invention may be labelled with a detectable label or may be conjugated with an effector molecule for example a drug e.g. an anti-bacterial agent, conventional procedures and the invention extends to such labelled antibodies or antibody conjugates.

The antibodies according to the invention have a diagnostic and/or therapeutic use. Thus for diagnostic use the antibodies may be employed to detect whether the stress protein is present in a host organism, to confirm whether the host has a particular bacterial infection, for example an infection due to a Gram-positive organism, expecially a Coryneform organism, particularly C.diphtheriae or C.jeikeium, for example in the diagnosis of septicaemias or endocarditis, and/or to monitor the progress of therapeutic treatment of such infections. Diagnostic methods of this type form a further aspect of the invention and may generally employ standard techniques, for example immunological methods such as enzyme-linked immunosorbent methods, radioimmuno-methods, latex agglutination methods or immunoblotting methods. Such tests generally bring into contact the antibody and host body fluid and detect any resulting complexed antibody.

Antibodies according to the inventon also have a therapeutic use in the treatment of bacterial infections, for example those due to Gram-positive bacteria, especially Coryneform organisms as just described, and may be used alone or conjugated to an effector molecule, [in the latter case to terget the effector molecule, e.g. an anti-bacterial agent to the infecting organism], optionally in combination with other pharmaceutical agents, such as other antibacterial or anti-fungal agents. For therapeutic use the antibody may be formulated in accordance with conventional procedures, for example with a pharmaceutically acceptable carrier or excipient, e.g. isotonic saline for administration at an appropriate dosage, depending on the nature of the infection to be treated and the age and condition of the patient.

A particularly useful antibody according to this aspect of the invention is that which recognises the peptide KVIRKNIVKKMIE (SEQ ID NO:1) and according to a further aspect of the invention we provide an antibody capable of recognising the peptide KVIRKNIVKKMIE (SEQ ID NO:1) or an analogue thereof for use in the treatment or diagnosis of bacterial infection.

If desired, mixtures of antibodies may be used for diagnosis or treatment, for example mixtures of two or more antibodies recognising different epitopes of a bacterial stress protein according to the invention, and/or mixtures of antibodies of a different class, e.g. mixtures of IgG and IgM antibodies recognising the same or different epitope(s) of a bacterial stress protein of the invention.

The stress proteins according to the inventon may be prepared by a variety of processes, using an appropriate bacteria cell culture, e.g. a C.jeikeium cell culture, as starting material. Thus, for example, suitable bacterial cells may be harvested, lysed and, after separation of the cell debris the resulting cell extract may be fractionated using conventional separation techniques such as ion exchange and gel chromatography and electrophoresis, and immunopurification methods, for example, affinity chromatography using an antibody capable of recognising the protein, for example and antibody capable of recognising the peptide KVIRKNIVKKMIE (SEQ ID NO.1). During the preparation the presence of the desired protein may be monitored using any appropriate standard analytical technique based, for example on an antibody capable of recognising an epitope on the protein, for example an antibody capable of recognising the peptide KVIRKNIVKKMIE (SEQ ID NO.1). Use of the above techniques can be expected to yield the stress protein in a purified form.

Alternatively, the protein may be cloned and expressed starting from an appropriate C.jeikeium genomic library and using standard screening and recombinant DNA techniques.

BRIEF DESCRIPTION OF THE DRAWINGS

In the following description various embodiments of the present invention are described with reference to the accompanying drawings in which.

The following Examples illustrate the invention.

EXAMPLE 1

The following reports the results of immunoblotting sera from patients with a C.jeikeium septicaemia or endocarditis and compares the data with immunoblots obtained from sera which were negative for the JK coryneform. [Jackman, P. J. H. and Pelezyneka, J., J. Gen. Microbiology (1986), 132, 1911–1915].

Patients

Controls—Sera were examined from 18 pyrexial neutropenic leukaemics where all cultures were negative for the JK coryneform. This included blood and those taken from any indwelling intravenous line.

Sepicaemias

Between two and five sequential sera were examined from 14 patients with C.jeikeium septicaemias. Thirteen of the 14 cases came from neutropenic patients who recovered on vancomycin therapy. Their pyrexia correspond with a blood culture positive with the C.jeikeium. Three of the cases had acute lymphatic leukaemia and the remaining 10 had acute myeloid leukaemia. The 14th case came from a patient who was admitted to an Intensive Therapy Unit following a road traffic accident. He was not neutropenic and his *C.jeikeium* septicaemia followed colonization of a long-term indwelling central line. He responded to vancomycin therapy.

Endocarditis

Case 15 came from a patient with ulcerative colitis with an intravenous feeding line which becane colonized by *C.jeikeium*. The patient subsequent developed endocarditis as judged by a positive echo-cardiogram and continuing pyrexia. Three sets of blood cultures grew the *C.jeikeium* and the patient gradually recovered after systemic vancomycin therapy.

Strain

A clinical isolate of the *C.jeikeium* obtained from a septicaemic case was used throughout.

Preparation of Protein Extracts

The *C.jeikeium* isolate was sub-cultured onto COLUMBIA BLOOD-AGAR (blood agar; Oxoid) and incubated at 35° C. for 48 hours aerobically. The plates were harvested with a loop in distilled water and the resulting cell suspension spun at 6000 g for 20 minutes. The pellet was re-suspended in its own volume of sterile distilled water and placed inside an Xpress. It was crushed at −20° C. and centrifuged at 12,000 G for 20 minutes. The supernatant was used in subsequent experiments and stored at −20° C. It was standardised to a protein concentration of 10 mg/ml.

Immunoblotting of Patients Sera

After heating with cracking buffer [2.6% sodium dodecyl sulphate, 1.3% 2-mercapto-ethanol, 6% glycerol, 0.2% bromophenol blue, 0.05% M Tris hydrochloride (pH 6.8)] at 10° C. for 2 minutes, 30 μg of the *C.jeikeium* pressate was loaded onto each well of a 10% polyacrylamide gel. Electrophoresis and transblotting were performed as described by Matthews, R. C. et al, [Lancet, 11 1415–1418 (1984); and J. Clin, Microbiol. 25, 230–237 (1987)]. The gel was transferred onto a nitrocellulose membrane in an LKB TRANSBLOTTER (a transblotting chamber for Western blotting; LKB Laboratories). The buffer contained methanol (20%), 25 mM Tris and 192 mM glycine at pH 8.3 and transfer was allowed to proceed at 25° C. for 45 minutes. The nitrocellulose paper was blocked in bovine-serum albumen (3%) in buffered saline (NaCl 0.9% and 10 mM Tris, pH 7.4) at 4° C. overnight. The nitrocellulose was then incubated at 35° C. for 2 hours with the patients serum diluted 1:10 in buffered saline containing bovine serum 3% albumin and 0.05% TWEEN 20 (polyoxyethylenesorbitan monolaurate). After washing 5 times for 30 minutes in 0.9% saline and 0.05% TWEEN 20 (polyoxyethylenesorbitan monolaurate), the nitrocellulose was incubated for one hour at 35° C. with alkaline phosphatase conjugated goat anti-human immunoglobulin M (IgM) or IgG (Sigma Chemical Co.). After washing again, the membranes were incubated for 15 minutes at 25° C. with buffer (100 mM Tris hydrochloride pH 9.5, 100 mM NaCl, 5 mM $MgCl_2$) containing a mixture of 66 μl/per 10 mls of nitro-blue tetrasolium (MBT 50 mg per ml in N,N-dimethylformamide 70%) and 33 μg per 10 mls of 5-bromo-4-chloro-3 indolylphosphate (BCIP 50 mg/ml in N,N-dimethylformamide 70%). The reaction was stopped by washing in water. All the immunoblots were examined and split into trace responses, [where a reflectance densitometer produced a trace with a height of less than 40 mm] and positive responses [where the height was greater than 40 mm].

Molecular weight markers were PRESTAINED RAINBOW MARKERS (prestained molecular weight markers; code RPN.756 Amersham International). These were myosin, 200 kDa, phosphorylase b, 92.5 kDa; bovine serum albumin, 69 kDa; ovalbumin, 46 kDa; carbonic anhydrase, 30 kDa; trypsin inhibitor, 21.5 kDa; and lysozyme, 14.3 kDa.

Results

The results from the 18 control patients are given in Table 1. Six bands were detected and the commonest antibody response was to the band at 110 kDa. Sequential sera were available in four of the patients where there was an antibody response and the patterns did not change over a period of at least two weeks. Trace and positive results [see above] were combined for this Table.

TABLE 1

Details of the antibody responses in control patients

| Apparent Molecular Weight (kDa) | IgM | IgG |
| --- | --- | --- |
| 170 | 3 | 3 |
| 154 | 0 | 1 |
| 110 | 4 | 3 |
| 86 | 0 | 1 |
| 70 | 0 | 4 |
| 60 | 1 | 0 |

Septicaemic Patients

Figure 1:
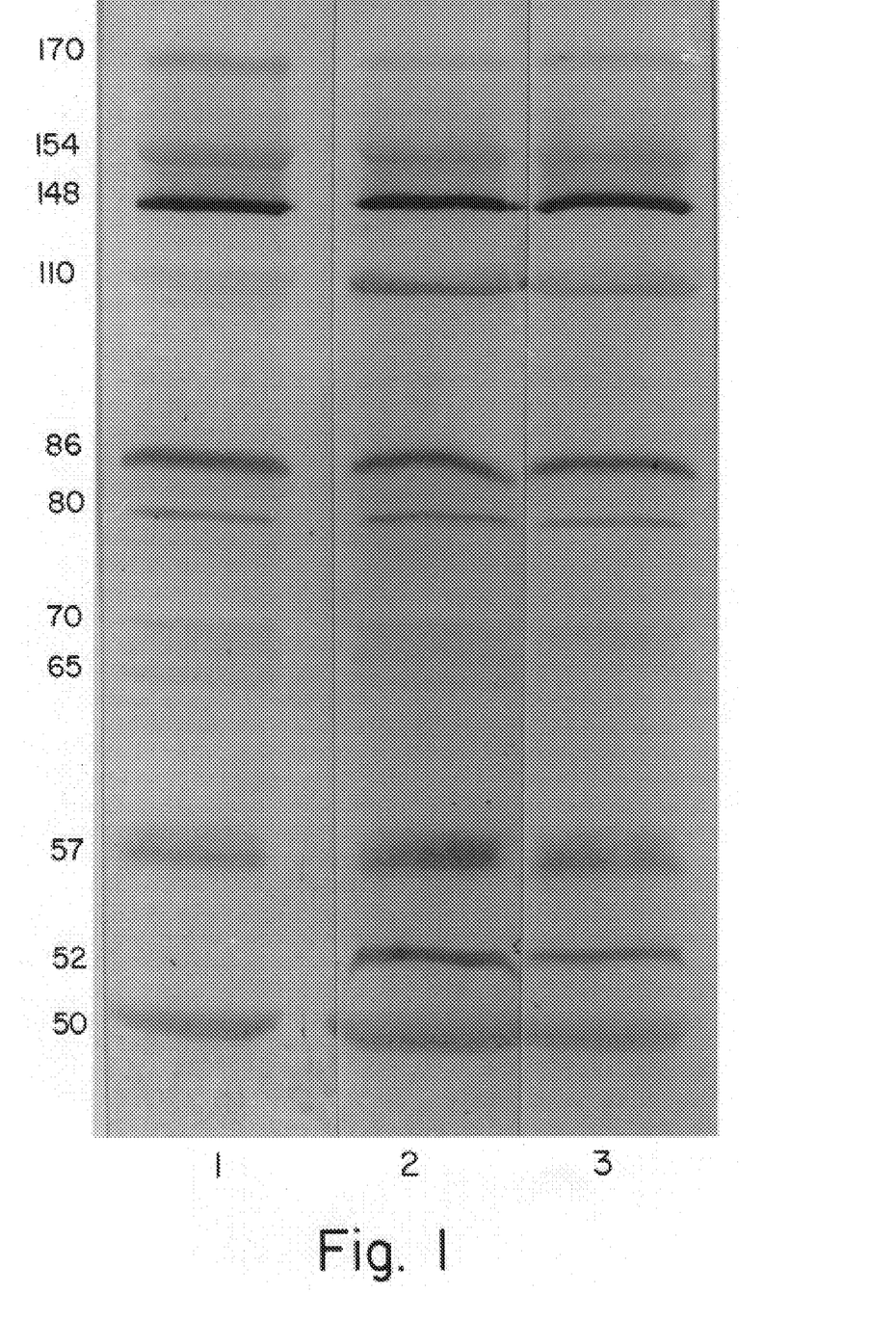
FIG. 1—shows sequential immunoblots of the IgG response to a C.jeikeium septicaemia in a patient who survived the infection.

The results from these are summarised in Tables 2 and 3. They are given according to four criteria. These are: a constant trace reaction, a constant positive reaction, an increase in brightness which is at least a doubling of intensity as measured by reflectance densitometry and finally the appearance of a new antigenic band. The results from the serum taken prior to *C.jeikeium* infection were compared to those after infection. IgM levels (Table 2) were static for the bands at 154, 86, 80, 70, 65, 60 and 43 kDa. A maximum of two patients showed changes in the bands at 170, 160, 158, 148 and 57 kDa. An increase in or the appearance of IgM against the bands at 110, 52 and 50 kDa were the most marked changes which occurred during infection. IgG levels (Table 3) showed a similar picture to IgM. Twelve patients developed a more pronounced antibody response to the band at 110 kDa. All the patients upon recovery produced IgG against the band at 52 kDa and an example of this is illustrated in FIG. 1. This patient was the road traffic accident and also slowed an increase in the serum level of IgG against the band at 110 kDa. Tract 1 is prior to septicaemia whilst tracks 2 and 3 were taken, respectively, just after the cessation of vancomycin therapy and five days later. Nine of the 14 patients also produced IgG against the 50 kDa band.

Figure 2:
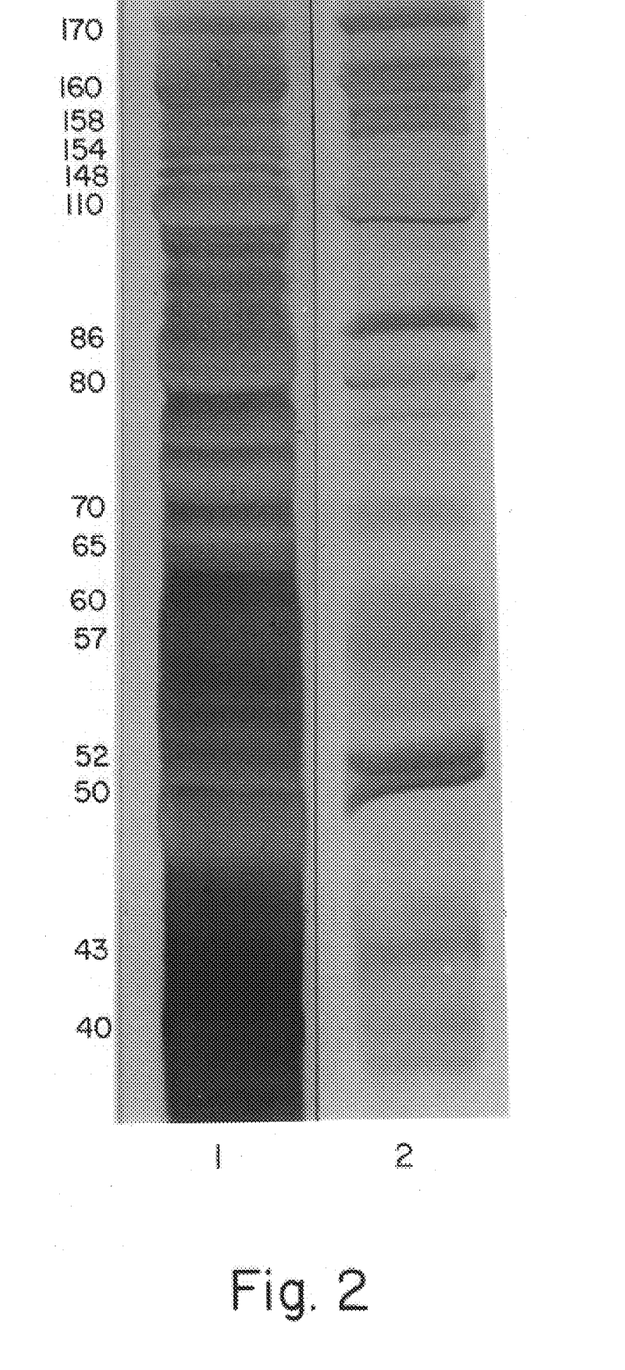
FIG. 2—shows an immunoblot of the IgM and IgG response to a C.jeikeium endocarditis in a patient who survived the infection.

The case of endocarditis (FIG. 2) had IgM and IgG against all the antigenic bands previously described for the septicaemic patients. The IgM response faded on successful treatment whilst the IgG increased to the 50 and 52 kDa bands.

Summary

The above results show that recovery from the septicaemia was associated with production of both IgM and IgG against antigenic bands of 50, 52 and 110 kDa. Antibody against the 110 kDa band was present in controls but the antibody against the 50 and 52 kDa bands was specific to those patients who had on-going or previous *C.jeikeium* infection. In the case of the *C.jeikeium* endocarditis recovery was also associated with sero-conversion to the 50 and 52 kDa bands. This illustrates the potential of using either of these antigens as the basis of a serodiagnostic test.

TABLE 2

Details of the IgM response in septicasmic patients to individual C. jeikeium bands

| Apparent Molecular Weight (kDa) | IgM Trace | Constant Positive | Increase in brightness | Appearance of band |
|---|---|---|---|---|
| 170 | 4 | 8 | 2 | |
| 160 | 2 | 2 | 1 | 1 |
| 158 | 3 | 1 | 1 | 1 |
| 154 | 3 | 1 | | |
| 148 | | 2 | 1 | |
| 110 | 3 | 3 | 5 | 3 |
| 86 | | 1 | | |
| 80 | | 1 | | |
| 70 | | 2 | | |
| 65 | | 2 | | |
| 60 | | | | |
| 57 | 1 | | | 1 |
| 52 | 2 | | | 7 |
| 50 | 1 | | | 3 |
| 43 | 1 | | | |
| 40 | | | | |

TABLE 3

Details of the IgG response in septicasmic patients to individual C. jeikeium bands

| Apparent Molecular Weight (kDa) | IgG Trace | Constant Positive | Increase in brightness | Appearance of band |
|---|---|---|---|---|
| 170 | 5 | 5 | 2 | 1 |
| 160 | 1 | 5 | 2 | |
| 158 | 2 | 2 | 1 | 1 |
| 154 | 2 | 2 | | |
| 148 | 1 | 1 | | |
| 110 | | 2 | 7 | 5 |
| 86 | 3 | 2 | | |
| 80 | 3 | 3 | | |
| 70 | 4 | 2 | 2 | |
| 65 | 3 | | 2 | 1 |
| 60 | 1 | | | |
| 57 | 1 | 1 | | |
| 52 | | | | 14 |
| 50 | | | | 9 |
| 43 | 1 | 1 | | |
| 40 | 1 | 1 | | |

EXAMPLE 2

Rabbit hyperimmune antisera against the peptide LKVIRKNIVKKMIE-Cys (SEQ ID NO:2) and against a pressate of C.albicans were raised using conventional methods [see for example Burnie, J., J. Immunol. Meth. (1985), 82, 267–280].

A murine monoclonal antibody was raised against LKVIRKNIVKKMIE-Cys-KLH (SEQ ID NO:4). Balb/c and CBA x Balb/c F1 mice were injected subcutaneously with 50 μg of immunogen in sterile complete Freund's Adjuvant and thereafter at intervals of 14 days, intraperitoneally with 50 μg immunogen in Incomplete Freund's Adjuvant until seroconvertion.

Fusion was performed 4 days after a final immunisation of 50 μg immunogen intravenously in sterile physiological saline. Fusion, hybridoma screening, clonal selection and antibody analysis were performed according to standard protocols, essentially as described by de St, Groth S. F. and Scheidegger D., J. Immunol. Methods 35, 1–21 (1980). Selected hybridomas were screened for activity against a C.albicans 47 Kd antigen by immunoblotting against C.albicans. Positive hybridomas were re-cloned and re-assayed.

Characterisation of Monoclonal Antibody

A novel hybridoma cell line (CA-STR7-1) obtained according to the above methods produced a monoclonal antibody which recognised both the C.albicans 47 Kd antigen and the antigen of approximately 92 Kd on immunoblots of C.albicans grown at 37° C., in both the yeast and mycelial forms. At 23° C. the 47 Kd antigen was visible but not the 92 Kd antigen with this monoclonal antibody.

Immunoblotting

The above rabbit antisera and monoclonal antibody were used to probe the C.jeikeium isolate (see Example 1).

Figure 3:
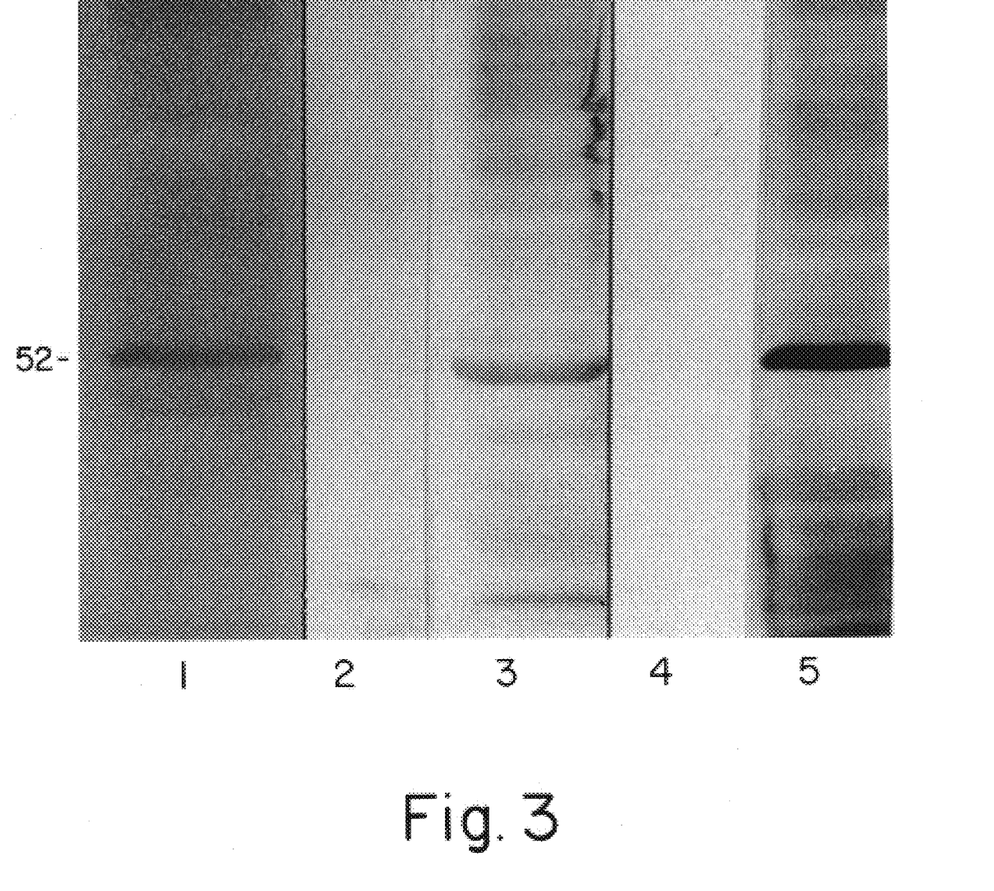
FIGS. 3 and 4—each show an immunoblot of a C.jeikeium isolate probed with rabbit antisera raised against a pressate of C.albicans and against the peptide LKVIRKNIVKKMIE-Cys (SEQ ID NO:2), and a monoclonal antibody raised against the same peptide, both before and after cross-absorption with peptide LKVIRKNIVKK-MIE (SEQ ID NO:3).
Figure 4:
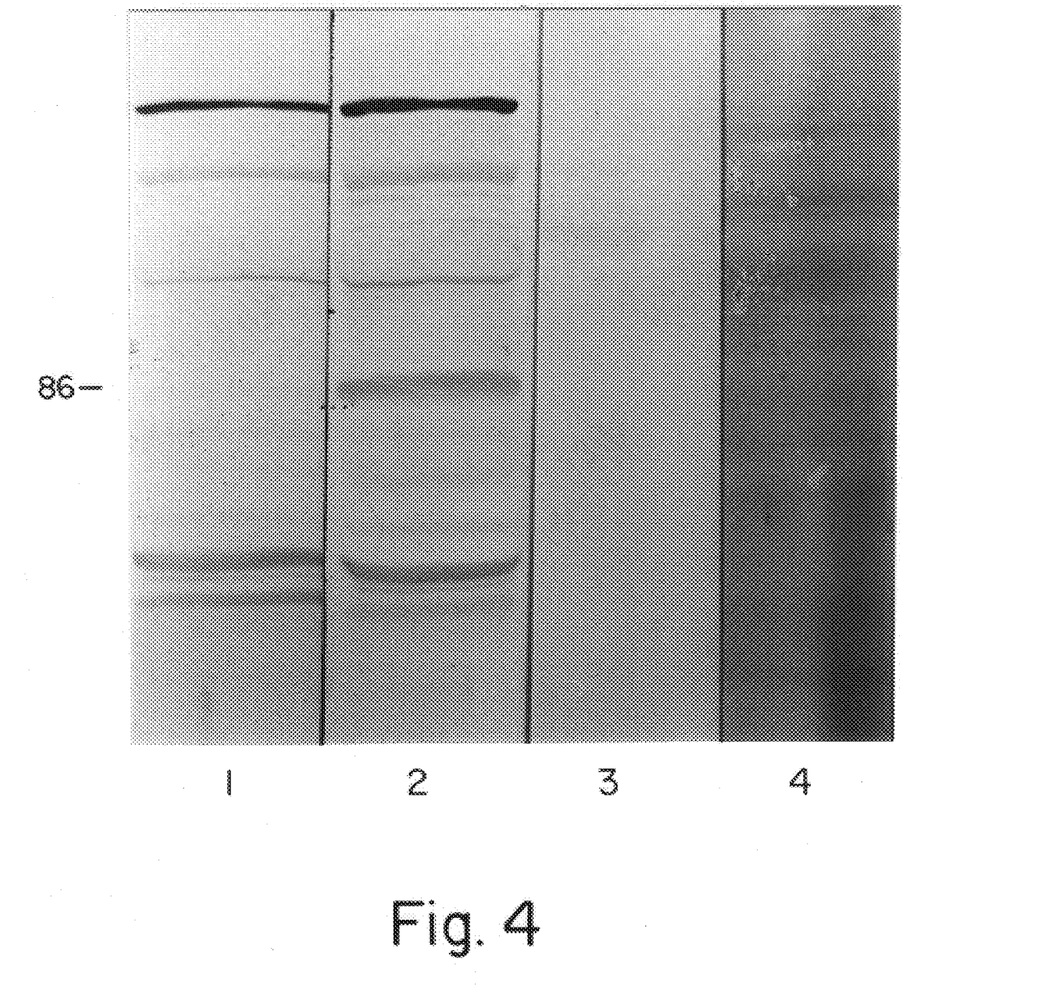

FIGS. 3 and 4 show immunoblots (see method in Example 1) obtained both before and after cross-absorption with the peptide KVIRKNIVKKMIE (SEQ ID NO.1) [1 mg/ml as follows]:

| | | |
|---|---|---|
| FIG. 3 | Tract 1 | Monoclonal against LKVIRKNIVKKMIE-Cys (SEQ ID NO: 2) crossreacting with 52 Kd band |
| | Tract 2 | Monoclonal against LKVIRKNIVKKMIE-Cys (SEQ ID NO: 2) after crossabsorption (no reaction) |
| | Tract 3 | Rabbit hyperimmune antiserum against LKVIRKNIVKKMIE-Cys (SEQ ID NO: 2) crossreacting with 52 Kd band |
| | Tract 4 | Rabbit hyperimmune antiserum against LKVIRKNIVKKMIE-Cys (SEQ ID NO: 2) after crossabsorption (no reaction) |
| | Tract 5 | Rabbit polyclonal hyperimmune against a pressate of C. albicans crossreacting with 52 Kd band. |
| FIG. 4 | Tract 1 | Rabbit hyperimmune antiserum against LKVIRKNIVKKMIE-Cys (SEQ ID NO: 2) after crossabsorption (no reaction with 86 Kd band). |
| | Tract 2 | Rabbit hyperimmune antiserum against LKVIRKNIVKKMIE-Cys (SEQ ID NO: 2) crossreacting with 86 KDa band. |
| | Tract 3 | Mouse monoclonal against LKVIRKNIVKKMIE-Cys (SEQ ID NO: 2) (no reaction) |
| | Tract 4 | Mouse monoclonal against LKVIRKNIVKKMIE-Cys (SEQ ID NO: 2) after crossabsorption (no reaction) |

The antisera and monoclonal antibody each detected the C.jeikeium, ilustrating their potential for use in a diagnostic test.

The rabbit hyperimmune serum crossreacted with bands at 86 Kd and 52 Kd. These were both neutralised by the peptide LKVIRKNIVKKMIE (SEQ ID NO:3) at 1 mg/ml. The monoclonal antibody reacted with the 52 Kd band and was neutralised by the corresponding peptide. The rabbit hyperimmune serum against a pressate of C.albicans crossreacted with the 52 Kd band.

I claim:

1. An isolated antibody or antibody fragment specific for at least one epitope of a purified Corynebacterial stress protein having an apparent molecular weight of about 86 Kd, said stress protein having the following features:

(1) being an antigen:

(2) inducing in patients with *Corynebacterium jeikeium* septicemia on recovery antibody to a 52 Kd breakdown product of the stress protein;

(3) inducing in patients with *Corynebacterium jeikeium* endocarditis antibody to a 52 Kd breakdown product of the stress protein;

(4) being cross reactive with a mouse monoclonal antibody against a peptide antigen consisting of KVIRKNIVKKMIE (SEQ ID NO:1); and (5) cross-reaction of the stress protein with said mouse monoclonal antibody is neutralized by the peptide consisting of KVIRKNIVKKMIE (SEQ ID NO.1).

2. The antibody or fragment thereof according to claim 1 which is a human antibody or fragment.

3. The fragment according to claim 2 which is selected from the group consisting of a single chain Fv, F(ab')$_2$, Fab', Fab and an Fv fragment.

4. The antibody or fragment according to claim 3 which is recombinant.

5. The antibody according to one of claims 1 or 2 which is a monoclonal antibody.

\* \* \* \* \*

UNITED STATES PATENT AND TRADEMARK OFFICE
CERTIFICATE OF CORRECTION

PATENT NO. : 5,985,277
DATED : November 16, 1999
INVENTOR(S) : Burnie

It is certified that error appears in the above-identified patent and that said Letters Patent is hereby corrected as shown below:

Title page, item [73] Assignee:

Please delete "The Victoria University of Manchester, Manchester, United Kingdom" and insert --NeuTec Phama plc, Manchester, United Kingdom--

Signed and Sealed this

Seventeenth Day of July, 2001

Attest:

NICHOLAS P. GODICI
Attesting Officer
Acting Director of the United States Patent and Trademark Office

UNITED STATES PATENT AND TRADEMARK OFFICE
CERTIFICATE OF CORRECTION

PATENT NO.   : 5,985,277
DATED        : November 16, 1999
INVENTOR(S)  : Burnie

It is certified that error appears in the above-identified patent and that said Letters Patent is hereby corrected as shown below:

Title page,
Item [73], Assignee: please delete "The Victoria University of Manchester, Manchester, United Kingdom" and insert -- NeuTec Pharma plc, Manchester, United Kingdom --

This certificate supersedes Certificate of Correction issued July 27, 2001.

Signed and Sealed this

Twenty-seventh Day of August, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Lys Val Ile Arg Lys Asn Ile Val Lys Lys Met Ile Glu
1               5                   10

(2) INFORMATION FOR SEQ ID NO:2:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Leu Lys Val Ile Arg Lys Asn Ile Val Lys Lys Met Ile Glu Cys
1               5                   10                  15

(2) INFORMATION FOR SEQ ID NO:3:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

Leu Lys Val Ile Arg Lys Asn Ile Val Lys Lys Met Ile Glu
1               5                   10

(2) INFORMATION FOR SEQ ID NO:4:

(i) SEQUENCE CHARACTERISTICS:
       (A) LENGTH: 16 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:4:

Leu Lys Val Ile Arg Lys Asn Ile Val Lys Lys Met Ile Glu Cys Xaa
1               5                   10                  15